US011000577B2

(12) United States Patent
Shivakumar

(10) Patent No.: US 11,000,577 B2
(45) Date of Patent: *May 11, 2021

(54) COMPOSITIONS AND METHODS FOR TREATING NEONATAL BILIARY ATRESIA

(71) Applicant: Children's Hospital Medical Center, Cincinnati, OH (US)

(72) Inventor: Pranav-Kumar Shivakumar, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/703,939

(22) Filed: Dec. 5, 2019

(65) Prior Publication Data

US 2020/0147187 A1 May 14, 2020

Related U.S. Application Data

(63) Continuation of application No. 15/577,453, filed as application No. PCT/US2016/033858 on May 24, 2016, now Pat. No. 10,532,087.

(60) Provisional application No. 62/170,261, filed on Jun. 3, 2015.

(51) Int. Cl.
| | |
|---|---|
| *A61K 38/57* | (2006.01) |
| *A61P 1/16* | (2006.01) |
| *A61K 45/06* | (2006.01) |
| *C07K 14/81* | (2006.01) |

(52) U.S. Cl.
CPC .............. *A61K 38/57* (2013.01); *A61K 45/06* (2013.01); *A61P 1/16* (2018.01); *C07K 14/8121* (2013.01)

(58) Field of Classification Search
None
See application file for complete search history.

(56) References Cited

U.S. PATENT DOCUMENTS

| | | | |
|---|---|---|---|
| 4,915,945 | A | 4/1990 | Pelzer et al. |
| 5,135,916 | A | 8/1992 | Sims et al. |
| 5,853,722 | A | 12/1998 | Rollins et al. |
| 5,939,389 | A | 8/1999 | Eisele et al. |
| 6,248,365 | B1 | 6/2001 | Romisch et al. |
| 6,355,245 | B1 | 3/2002 | Evans et al. |
| 6,753,164 | B2 | 6/2004 | Ni et al. |
| 7,053,176 | B1 | 5/2006 | Hafner et al. |
| 8,546,548 | B2 | 10/2013 | Teschner et al. |
| 10,125,191 | B2 | 11/2018 | Wang |
| 10,471,142 | B2 | 11/2019 | Basta et al. |
| 10,532,087 | B2 | 1/2020 | Shivakumar |
| 2015/0104445 | A1 | 4/2015 | Uknis et al. |

FOREIGN PATENT DOCUMENTS

| | | |
|---|---|---|
| WO | WO 2005/112989 A1 | 12/2005 |
| WO | WO 2007/073186 A2 | 6/2007 |
| WO | WO 2016/196070 A1 | 12/2016 |
| WO | WO 2016/209956 A1 | 12/2016 |

OTHER PUBLICATIONS

Definition of biliopathy downloaded from https://en.wiktionary.org on Nov. 20, 2020 (Year: 2020).*
Biliary Atresia downloaded from https://www.hopkinsmedicine.org on Nov. 20, 2020 (Year: 2020).*
Cole, S.P.C. et al., "The EBV-Hybridoma Technique and Its Application to Human Lung Cancer," *Monoclonal Antibodies and Cancer Therapy*, Alan R. Liss, Inc., New York, 1985, pp. 77-96, 22 pgs.
Floreani, A., et al., "New Therapies for Primary Biliary Cirrhosis," Clinic Rev Allerg Immunol, 2015, 48:263-272, 10 pgs.
Harlow, E., Ed., et al., "Antibodies: A Laboratory Manual," Cold Spring Harbor Laboratory Press, 1988, Table of Contents only, 9 pgs.
Harlow, E., Ed., et al., "Using Antibodies: A Laboratory Manual," Cold Spring Harbor Laboratory Press, 1999, Table of Contents only, 5 pgs.
Kohler, G., et al., "Continuous cultures of fused cells secreting antibody of predefined specificity," Nature, 1975, 256(5517):495-497, 3 pgs.
Kozbor, D., et al., "The production of monoclonal antibodies from human lymphocytes," Immunology Today, 1983, 4(3):72-79, 8 pgs.
Saidi, R.F., et al., "Liver Ischemia/Reperfusion Injury; an Overview," Journal of Investigative Surgery, 2014, 27:366-379, 14 pgs.
Soualmia, F., et al., "Serine protease inhibitors to treat inflammation: a patent review (2011-2016)" Expert Opinion on Therapeutic Patents, 2018, 28(2):93-110, 18 pgs.
International Search Report and Written Opinion dated Aug. 25, 2016 for Application No. PCT/US2016/033858, 13 pgs.
Supplementary European Search Report and Written Opinion dated Jan. 9, 2019 for Application No. EP 16804000.4, 7 pgs.
U.S. Appl. No. 62/170,261, filed Jun. 3, 2015.
Arnon, R., et al., "Liver Transplantation for Children With Biliary Artesia in the Pediatric End-Stage Lever Disease Era: The Role of Insurance Status," Liver Transplantation, 2013, 19(5):543-550, 8 pgs.
Copeland, D.A., et al., "Systemic and local anti-C5 therapy reduces the disease severity in experimental autoimmune uveoretinitis," Clinical and Experimental Immunology, 2009, 159(3):303-314, 12 pgs.
Costa, C., et al, "Role of complement component C5 in cerebral ischemia/reperfusion injury" Brain Research, 2006, 110(1):142-151, 10 pgs.

(Continued)

*Primary Examiner* — Christina Bradley
(74) *Attorney, Agent, or Firm* — Frost Brown Todd LLC; Nicole M. Tepe

(57) ABSTRACT

Disclosed are methods and compositions for treatment of a subject having a biliary disorder. The methods include administering a therapeutically effective amount of a serine protease inhibitor to a subject in need thereof. The biliary disorder may include biliary atresia, a biliopathy, Primary Biliary Cirrhosis (PBC), Primary Sclerosing Cholangitis (PSC), and combinations thereof. In certain aspects, the serine protease inhibitor may be a protease inhibitor rC1 Inhibitor.

8 Claims, No Drawings

(56) References Cited

OTHER PUBLICATIONS

Horiuchi, T., et al., "Complement-targeted therapy: development of C5- and C5a-targeted inhibition," Inflammation and Regeneration, 2016, 36:11, 5 pgs.
Karakayali, H., et al., "Liver Transplantation for Biliary Atresia," Transplantation Proceedings, 2008, 40(1):231-233, 3 pgs.
Lee, J.Y., et al., "Cholangitis in children with biliary atresia: Health-care resource utilisation" Journal of Paediatrics and Child Health 2013, 50:196-201, 6 pgs.
Lilly, J.R., et al., "Hepatic portoenterostomy (the Kasai operation) for biliary atresia," Surgery, 1975, 78(1):76-86, 11 pgs.
Liu, L., et al., "Sublytic C5b-9 Complexes Induce Apoptosis of Glomerular Mesangial Cells in Rats with Thy-1 Nephritis through Role of Interferon Regulatory Factor-1-dependent Caspase 8 Activation," The Journal of Biological Chemistry, 2012, 287(20):16410-164231 14 pgs.
Mieli-Vergani, G., et al., "Biliary atresia," Semin Immunopathol, 2009, 31(3):371-381, 11 pgs.
Petersen, C., et al., "Postoperative High-Dose Steroids Do Not Improve Mid-Term Survival With Native Liver in Biliary Atresia," Am J Gastroenterol, 2008, 103(3):712-719, 8 pgs.
Pfister, J., et al., "Activate Complement Components Target Hepatobiliary System in Experimental Biliary Atresia," Abstract 483, Presented at the Digestive Diseases Week, McCormich Place, Chicago, IL, May 7-10, 2011, p. S-892, 1 pg.
Pfister, J., et al., "Complement Receptor C5aR Regulates Hepatic Inflammatory Response, Epithelial Injury and Duct Obstruction in Biliary Atresia," Abstract 106, Hepatology, Oct. 2011, 54(4 Suppl):411A-412A, 2 pgs.
Ramachandran, P., et al., "C5aR targets immune and epithelial cell compartments in experimental and human biliary atresia," Abstract 1698, Hepatology, 2015, 62(1 Suppl):1036A-1037A, 2 pgs.
Ramachandran, P., et al., "Immune and target cell C5AR1 expression differentiates clinical stages in biliary atresia," Abstract # P-224, Transplantation, 2016, 100(5S):S201, 1 pg.
Saxena, V., et al., "Dendritic Cells Regulate Natural Killer Cell Activation and Epithelial Injury in Experimental Biliary Atresia," Sci Transl Med, 2011, 3(102):102ra94, 23 pgs.
Schmitt, J., et al., "Complement factor C5 deficiency significantly delays the progression of biliary fibrosis in bile duct-ligated mice," Biochemical and Biophysical Research Communications, 2012, 418:445-450, 6 pgs.
Shivakumar, P., et al., "Effector role of neonatal hepatic CD8+ lymphocytes in epithelial injury and autoimmunity in experimental biliary atresia," Gastroenterology, 2007, 133(1):268-277, 17 pgs.
Shivakumar, P., et al., "Neonatal NK cells target the mouse duct epithelium via Nkg2d and drive tissue-specific injury in experimental biliary atresia," The Journal of Clinical Investigation, 2009, 119(8):2281-2290, 10 pgs.
Teckman, J., "Selected Summary," Journal of Pediatric Gastroenterology and Nutrition, 2009, 48(1):115-116, 2 pgs.
Wang, Y., et al., "Anti-C5 monoclonal antibody therapy prevents collagen-induced arthritis and ameliorates established disease," PNAS USA, 1995, 92(19):8955-8959, 5 pgs.
International Search Report and Written Opinion dated Jun. 11, 2019 for Application No. PCT/US2019/027177, 12 pgs.

* cited by examiner

COMPOSITIONS AND METHODS FOR TREATING NEONATAL BILIARY ATRESIA

CROSS-REFERENCE TO RELATED APPLICATIONS

This application is a continuation of U.S. patent application Ser. No. 15/577,453, entitled "Compositions and Methods for Treating Neonatal Biliary Atresia," filed Nov. 28, 2017 and issued as U.S. Pat. No. 10,532,087 on Jan. 14, 2020, which claims priority to and benefit of International Application No. PCT/US2016/033858, entitled "Compositions and Methods for Treating Neonatal Biliary Atresia," filed May 24, 2016, which claims the benefit of and priority to U.S. Provisional Application No. 62/170,261, filed Jun. 3, 2015, the contents of which are incorporated by reference in their entirety for all purposes.

BACKGROUND

Biliary Atresia (BA) is a pediatric liver disease restricted to newborn infants with no known medical treatment. BA is a rare neonatal disease manifesting only in the first few weeks of life characterized by ascending obstruction of the biliary tree resulting in severe cholestasis and rapidly progressing biliary cirrhosis. The common histopathological picture is one of inflammatory damage to the intra- and extrahepatic bile ducts with sclerosis and narrowing or obliteration of the biliary tree. BA is a rapidly progressing obliterative disease of the extra- and intra-hepatic bile ducts and represents an extreme spectrum of neonatal cholestasis. Children who develop BA are born jaundice-free; however, within the first weeks of life, the extrahepatic biliary tree develops inflammation leading to duct obstruction and loss of bile flow.

Untreated, this condition leads to cirrhosis and death within the first years of life. BA remains the most common indication for pediatric liver transplantation worldwide. The incidence of B.A is approximately 1:10-15,000 of live births and is classified as a rare disease by NORD (National Organization of Rare Disorders) end NODK, Children who develop BA are born jaundice-free; however, within the first weeks of life, the extrahepatic biliary tree develops inflammation leading to duct obstruction and loss of bile flow. The baby suffers from acholic (chalk-colored) stools, yellowing of skin, enlarged liver and spleen, ascites develops with rapidly progressing liver injury and cirrhosis, and the baby suffers from loss of weight, becomes irritable and has worsening jaundice. Infants with BA are severely ill and may face developmental challenges even after liver transplantation. Infants affected by BA represent an extreme spectrum of neonatal cholestasis and show progressive jaundice and growth retardation. Because of the severe clinical manifestations and limited therapeutic options, most infants progress to end-stage liver cirrhosis, portal hypertension and liver failure eventually needing liver transplantation.

Intraoperative cholangiogram is the only mechanism available for a definitive diagnosis of BA. Because of the progressive nature of the disease, infants, at the time of diagnosis present with a scarred extrahepatic bile duct with varying degrees of intrahepatic inflammation and fibrosis. Surgical intervention by Kasai portoenterostomy (KPE) is the only treatment option, which removes the entire fibrosed biliary tree and surgically recreates an intestinal anastomosis to establish bile flow. While the postsurgical medical management combines nutrition, antibiotics, choleretics, and possibly anti-inflammatory medications, the impact of these practices on the clinical outcome is unclear, and there are no medical therapies available to prevent ongoing liver injury following a Kasai procedure. Further, infants having a "failed Kasai" will require a liver transplant in infancy to survive, and infants diagnosed too late have too much liver damage to benefit from Kasai and will require early transplant. These two groups of patients encompass about ⅓ to more than half of the BA population.

Post-operative complications are also significant in that some patients, even after successful bile drainage, can still experience cholangitis and succumb to infection. Despite the clinical success of resolving extrahepatic bile duct manifestations of the disease, progression of the liver disease involving intrahepatic bile ducts continue in a majority of children resulting in cirrhosis, with only 13-50% of patients alive with native liver by 2 years of age. In infants progressing to end-stage cirrhosis, liver transplantation is the only option—assuming an average cost of $200-300K per transplant, the economic burden to treat children with BA is approximately –$134 million annually placing significant strain on the affected families as well as on health-care resources and service utilization costs. This is further compounded by a complete lack of medical interventions.

The current nontransplant treatment strategies are at best palliative and primarily make use of steroids in the immediate post-operative period due to their anti-inflammatory properties. However, the role of corticosteroids in improving bile flow is controversial. Indeed, several clinical trials including the most recent and extensive trial of corticosteroid therapy in the US following Kasai (ChiLDREN; START trial: NCT00294684) showed that steroids alone do not prevent the need for liver transplantation. Outcomes from most of these trials strongly suggest the existence of inflammatory footprints beyond the immune-suppressive capacity of, or pathways regulated by steroids. Of significance, in the current pediatric end-stage liver disease (PELD) system, children with BA face the risk of not receiving a liver in a safe and timely manner.

Thus, identification of temporo-spatial effectors of hepatobiliary injury is of paramount significance towards designing novel treatment strategies. The instant invention seeks to address one or more of the aforementioned needs in the art.

BRIEF SUMMARY

Disclosed are methods and compositions for treatment of a subject having a biliary disorder. The methods include administering a therapeutically effective amount of a serine protease inhibitor to a subject in need thereof. The biliary disorder may include biliary atresia, a biliopathy, Primary Biliary Cirrhosis (PBC), Primary Sclerosing Cholangitis (PSC), and combinations thereof. In certain aspects, the serine protease inhibitor may be a protease inhibitor rC1 Inhibitor.

DETAILED DESCRIPTION

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "therapeutically effective amount" means the total amount of an active component sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

The instant disclosure relates to methods and compositions for the treatment of biliary atresia and associated pathologies such as inflammation, by targeting the complement and intrinsic coagulation (contact system) pathways, such as via administration of a protease inhibitor, for example, rC1INH. The intended targets may be the molecules that make up the complex network of activated components of the classical and alternative pathways of complement activation, proteases of the fibronolytic/clotting and kinin pathways, and the leukocyte adhesion molecules. The protease inhibitor therapy is targeted to a) attenuate ongoing liver inflammation and/or b) promote regenerative responses in liver and bile duct cells. In another aspect, the therapy disclosed herein may be an alternative to liver transplant.

The disclosure further relates to treatment of biliary atresia, which manifests in the first few weeks of life, characterized by ascending obstruction of the biliary tree resulting in severe cholestasis and rapidly progressing biliary cirrhosis, which may include inflammatory damage to the intra- and extrahepatic bile ducts with sclerosis and narrowing or obliteration of the biliary tree. The instant disclosure relates to methods of ameliorating or, in some aspects, reversing one or more such conditions associated with biliary atresia.

Exploring global microarray data generated using EHBDs from control and diseased neonatal mice, Applicant has identified an "activation circuitry" involving activated complement components (C1qa/b/c, C1r, C1s, C3b, Cfb, Properdin, C6, Masp2, Mbl1, Mbl2), proteases of the fibrinolytic/clotting (F3, F9, F11, F12, Cmklr1, Plau, Plaur, Plat, Fga, Fgg, Serpine1) and kinin (Bdkrb1, Kng1, Kng2, Klk1, Klk1b4, Klk1b5, Klk1b21) pathways and Selectins (Sele, Sell, Selp, Selplg). This increased pro-inflammatory milieu was associated with decreased levels of complement regulatory proteins including Serping1 (C1INH), Serpine1, Daft, CD55, CD46, CD59a, CD59b, Cfh, Tfpi, C4 bp, Clu, Vtn and Crry. Applicant further investigated microarray data of livers from infants with BA and showed increased levels of PLAU, PLAUR, PLAT, BDKRB1, BDKRB2, SELL and SELP and significantly reduced levels of SERPING1 (C1INH), CFI, C4BPA, C4BPB, CFH, CR1, VTN and CLU. Such an ectopic activation of complement, coagulation and fibrinolysis systems in the same microenvironment has the potential to initiate autoimmune disorders. To counter these multifactorial but specific changes in gene expressions, Applicant identified C1 Inhibitor (C1INH; SERPINGI) as a candidate molecule capable of targeting these exorbitantly altered activation pathways.

C1-inhibitor (also called C1 esterase inhibitor or C1INH) is a protease inhibitor belonging to the serpin superfamily, and is described in, for example, US Patent Publication No. 2014/0234293. C1-inhibitor inhibits the complement system to prevent spontaneous activation. C1-inhibitor has a 2-domain structure. The C-terminal serpin domain is similar to other serpins, and is responsible for its inhibitor activity, The N-terminal domain is not essential for its inhibitory activity. C1-inhibitor is highly glycosylated, hearing both N- and O-glycans. The N-terminal domain is especially heavily glycosylated. Human C1-inhibitor is encoded by the SERPING1 gene. C1-INH not only regulates classical complement pathway through inactivation of C1r and C1s and removal of entire C1 complex, alternative complement pathway by interacting with C3b and inactivating MASP-1 and MASP-2 proteases of the lectin pathway, but also potently inhibits factor XI, thrombin, factor XII, plasma kallikrein, plasmin and tissue plasminogen activator. C1INH also binds to type IV collagen, laminin, entactin and fibrinogen and interacts with circulating neutrophils, macrophages and endothelial cells and binds to E- and P-selectins inhibiting leukocyte rolling and transmigration. In vivo, C1INH has suppressive activities on pro-inflammatory cytokines IL-1, TNFa, IFNg and IL-6 as well as generation of leukotrienes, prostaglandins and other eicosanoid molecules. The broad-spectrum activities of C1INH have beneficial roles in several inflammatory diseases including myocardial, brain and skeletal muscle ischemia-reperfusion injuries, vascular leak, bacterial sepsis and endotoxin shock, hyperacute transplant rejection, myocardial infarction, cardiopulmonary bypass, etc.

Without intending to be limited by theory, Applicant has found that pathogenic events appeared to suggest that some of the inflammatory circuits that evolved within and initiated EHBD injury continue to perpetuate sustained liver damage even after successful KPE. Using a neonatal mouse model of rotavirus (RRV)-induced experimental BA that efficiently recapitulates human disease, Applicant has linked activation of the complement system cellular responses involving NK, T- and dendritic cells to bile duct epithelial injury, inflammation and atresia.

Disclosed are methods of treating a subject having a biliary disorder. The method may comprise the step of administering a therapeutically effective amount of a serine protease inhibitor to the subject in need thereof. Applicant has found that some of the inflammatory circuits that evolved within and initiated EHBD injury continue to perpetuate sustained liver damage even after successful KPE. Using a neonatal mouse model of rotavirus (RRV)-induced experimental BA that efficiently recapitulates human disease, Applicant has definitively linked activation of the inflammatory circuits to epithelial injury, duct inflammation and atresia. Additionally, the cellular responses involving NK, T- and dendritic cells have been linked by Applicant to bile duct pathogenesis. Applicant has further identified an activation circuitry involving the Complement proteins, a dominant defense mechanism of the newborn immune repertoire. Global analysis of microarray data generated using extrahepatic bile ducts from control and diseased neonatal mice has revealed an enhanced signature for activated complement components (C1r, C1s, Cfb, C4a, C4b, Properdin, C1qa, C1qb, C1qc), proteases of the fibrinolytic clotting (F3, F9, F11, F12, Klk1, Cmklr1, Plau, Plaur, Plat, Serpine1, Fibrinogen) and kinin (bradykinin receptor 2, Bdkrb2) pathways and Selectins (Sele, Sell, Selp, Selplg). This increased proinflammatory milieu initiated as a result of biliary inflammation is associated with decreased levels of complement regulatory proteins (Serping1 (C1Inh), CfH, Cfi, CD59, Daf2, CD46, Vtn)—the cardinal inhibitors of complement and contact system activation. Such a phenomenon has the potential to greatly compromise the fine-tuned innate immune molecular and cellular responses resulting in autoimmune diseases including SLE, AMD, PNH, aHUS, etc. Applicant identified C1INH as a candidate molecule targeting the complement/contact systems and the Selectins all exorbitantly increased in biliary atresia. Furthermore, a similar signature is also operative in livers of infants with BA. Probing microarray data, Applicant found significantly reduced levels of key complement regulatory factors including SERPING1 (C1INH), CFI, C4BPA, C4BPB, CFH, CR1, VTN and CLU while expressions of PLAU, PLAUR, PLAT, BDKRB1, BDKRB2, SELL and SELP increased in patients with BA. A corresponding decrease in fibrinogen genes, FGA, FGB and FGG was also evident, reflecting progressive liver disease. Based on the preliminary data identifying increased signatures of C1INH targets, Applicant's central hypothesis is that augmenting C1INH levels attenuates hepatobiliary injury and improves disease-free survival.

In one aspect, the biliary disorder may be biliary atresia, a biliopathy, Primary Biliary Cirrhosis (PBC), Primary Sclerosing Cholangitis (PSC), and combinations thereof.

In one aspect, the serine protease inhibitor may be a protease inhibitor such as, for example, rC1 Inhibitor (rC1INH/SERPING1). The terms "C1 Inhibitor," "C1 esterase Inhibitor," and "C1-INH" refer to the proteins or fragments thereof that function as serine protease inhibitors to prevent spontaneous activation of circulating proteases associated with the complement system, preferably proteases C1r and C1s, as well as MASP-1 and MASP-2. In addition, C1-INH can serve as an anti-inflammatory molecule that reduces the selectin-mediated leukocyte adhesion to endothelial cells. C1-INH as used here can be a native serine protease inhibitor or active fragment thereof, or it can comprise a recombinant peptide, a synthetic peptide, a peptide mimetic, or a peptide fragment that provides similar functional properties—e.g., the inhibition of proteases C1r and C1s, and/or MASP-1 and MASP-2. For further disclosure regarding the structure and function of C1-Inhibitor, see U.S. Pat. Nos. 4,915,945; 5,939,389; 6,248,365; 7,053,176; and WO 2007/073186, which are hereby incorporated in their entirety. Commercially available products comprising C1-inhibitor are, e.g. plasma-derived CINRYZE® (Viropharma), recombinant RUCONEST® or RHUCIN® (both Pharming), and plasma-derived BERINERT® (CSL Behring). BERINERT® is indicated for treatment of hereditary angioedema and congenital deficiencies. Production of Immunoglobulin and C1-Inhibitor. In various embodiments, C1-Inhibitor can be produced according to methods known to one of skill in the art. For example, plasma-derived C1-INH can be prepared by collecting blood plasma from several donors. Donors of plasma should be healthy as defined in the art. For example, the plasma of healthy donors can be pooled and optionally further processed. An exemplary process for preparing plasma-derived immunoglobulin can be found in US Application 2010/0330071 A1.

Techniques for the production of non-plasma-derived antibodies and fragments that bind active complement fragments are well known in the art and described in, e.g. Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. Also, transgenic animals may be used to express fully human antibodies or fragments thereof. For the preparation of monoclonal antibodies, any technique that provides antibodies produced by continuous cell line cultures can be used. Examples for such techniques include the hybridoma technique originally described by Kohler and Milstein, Nature 256: 495-497 (1975) further developed by the art to produce human antibodies. Also included are the trioma technique, the human B-cell hybridoma technique (Kozbor, Immunology Today 4: 72 (1983)), and the EBV-hybridoma technique to produce human monoclonal antibodies (Cole et al., Monoclonal Antibodies and Cancer Therapy, Alan R. Liss, Inc. (1985), 77-96). The non-plasma-derived antibodies may be expressed in cells, e.g. antibody nucleic acid constructs may be transfected and/or transduced via, amongst others, viruses or plasmid vectors. Other recombinant techniques for production in small or large scale may also be used. Methods for preparing C1-INH are known in the art. For example, a process for producing C1-inhibitor for therapeutic purposes is disclosed in U.S. Pat. No. 4,915,945, the disclosure of which is hereby incorporated in its entirety. Alternatively, in some embodiments C1-INH can be collected and concentrated from natural tissue sources using techniques known in the art. Commercially available products comprising C1-inhibitor are, e.g. plasma-derived Cinryze® (Shire), recombinant Ruconest® or Rhucin® (both Pharming), and plasma-derived BERINERT® (CSL Behring) Recombinant C1-INH can be prepared by known methods.

In one aspect, the administration step may attenuate and/or reverse hepatobiliary injury, for example, one or more of intrahepatic and/or hepatobiliary inflammation, intrahepatic and/or hepatobiliary fibrosis, cholangiopathy, periductal inflammation, fibrosis, ballooning degeneration, confluent necrosis, portal inflammation, lobular inflammation, bile duct injury, bile duct fibrosis, portal and and/or pericellular bile duct fibrosis, and combinations thereof, in a subject in need of such treatment.

In one aspect, the administration step may promote a regenerative response in a liver and/or a bile duct cell in a subject having a biliary disorder.

In one aspect, the administration step may preserve, restore, or improve liver function in a subject having a biliary disorder.

In one aspect, the administration step may reduce or eliminate the need for a liver transplant in a subject having a biliary disorder.

In one aspect, the administration step may occur after the subject has undergone a Kasai procedure, for example, wherein a first dose is administered within 3-5 days of said procedure. A second dose may be administered at a second time point, for example, approximately 5 to 30 days, or from about 10 to 20 days, or about two weeks following the procedure. In other aspects, a third dose may be administered. The third dose may be administered at a time point of about 60 to 90 days following the Kasai procedure, or about 70 to 80 days following the Kasai procedure.

In one aspect, the serine protease inhibitor may be administered at a dose of from about 1 mg/kg to about 10 mg/kg.

In one aspect, the serine protease inhibitor may be administered in an amount sufficient to reduce serum biomarkers of liver injury selected from ALT, AST and/or Bilirubin.

In one aspect, the serine protease inhibitor may be administered until improvement in a phenotypic outcome occurs, for example, a phenotypic outcome such as attenuation or reversal of inflammation and/or fibrosis progression.

In one aspect, the serine protease inhibitor may be administered intravenously and/or subcutaneously.

In one aspect, IVIG may be co-administered with the serine protease inhibitor, for example, about 3 to about 5 days after the procedure.

Compositions

In one aspect, a composition comprising a therapeutically effective amount of a serine protease inhibitor and a pharmaceutically acceptable carrier is disclosed. In a further aspect, a composition consisting essentially of a therapeutically effective amount of a serine protease inhibitor and a pharmaceutically acceptable carrier is disclosed.

The composition may comprise a serine protease inhibitor, for the treatment of a biliary disorder in an individual, for example wherein the biliary disorder is selected from biliary atresia, a biliopathy, Primary Biliary Cirrhosis (PBC), Primary Sclerosing Cholangitis (PSC), and combinations thereof.

The serine protease inhibitor may be a protease inhibitor rC1 Inhibitor as disclosed herein.

The composition may attenuate and/or reverse hepatobiliary injury, for example, one or more of intrahepatic and/or hepatobiliary inflammation, intrahepatic and/or hepatobiliary fibrosis, cholangiopathy, periductal inflammation, fibrosis, ballooning degeneration, confluent necrosis, portal inflammation, lobular inflammation, bile duct injury, bile duct fibrosis, portal and and/or pericellular bile duct fibrosis, and combinations thereof, in a subject. The composition may further promote a regenerative response in a liver and/or a bile duct cell in a subject. In other aspects, the composition may preserve, restore, or improve liver function in a subject. In further aspects, the composition may reduce the need for a liver transplant in a subject.

The compositions may contain a serine protease inhibitor in an amount greater than about 0.5 ng/ml, or greater than about 1.0 ng/ml. In other aspects, a serine protease inhibitor may be present in an amount of from about 0.1 mg/mL to about 250 mg/mL, or from about 1 mg/mL to about 200 mg/mL, or from about 5 mg/mL to about 100 mg/mL, or from about 25 mg/mL to about 50 mg/mL. In a yet further aspect, a serine protease inhibitor may be present in an amount greater than about 250 mg/mL.

The composition may be formulated for subcutaneous administration to a subject or intravenous administration to a subject.

In one aspect, the composition may further comprise a buffer selected from citrate buffer, acetate buffer, bicarbonate buffer, phosphate buffer and combinations thereof.

The pharmaceutical formulations suitable for injectable use may include sterile aqueous solutions (where water soluble) or dispersions and sterile powders for the extemporaneous preparation of sterile injectable solutions or dispersion. In all cases, the form is ideally sterile and be fluid. In one aspect, the formulation may contain preservation agents for preventing contamination by microorganisms such as bacteria and fungi. The carrier may be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like.

The formulations may include isotonic agents, for example, sugars or sodium chloride. Prolonged absorption of the injectable compositions can be brought about by the use in the compositions of agents delaying absorption, for example, aluminum monosterate and gelatin. Sterile injectable solutions may be prepared with several of the other ingredients enumerated above, followed by filter or terminal sterilization. Generally, dispersions may be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation may be vacuum dried and the freeze-drying technique may be used to yield a powder of the active ingredient plus any additional desired ingredient from previously sterile-filtered solution thereof.

The formulation may contain one or more excipients. Pharmaceutically acceptable excipients which may be included in the formulation are buffers such as citrate buffer, phosphate buffer (such as, for example, monobasic sodium phosphate, dibasic sodium phosphate and combinations thereof), acetate buffer, bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers.

In certain aspects, the formulations may comprise an excipient selected from the group consisting of polyethylene glycol (PEG), PEG-400, arginine, arginine and glutamic acid, proline, gamma-cyclodextrin and combinations thereof.

In certain aspects, the buffer and/or excipient may be present in the formulation at a concentration of between about 1 and about 50% weight/volume (w/v), or between about 2 and about 40% w/v, or between about 3 and about 30% w/v, or between about 4 and about 20% w/v, or between about 5 and about 10% w/v.

In certain aspects, the buffer and/or excipient may be present in the formulation at a concentration of between about 1 and about 500 mM, or between about 10 and about 400 mM, or between about 20 and about 300 mM, or between about 30 and about 250 mM, or between about 40 and about 200 mM, or between about 50 and about 150 mm, or between about 60 and about 100 mM.

The formulation also may contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

For lyophilization of protein and chaperone preparations, the protein concentration may be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

The route of administration may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations may be by periodic injections of a bolus of the preparation, or may be administered by intravenous or intraperitoneal administration from a reservoir which is external (e.g., an i.v. bag) or internal (e.g., a bioerodable implant, a bioartificial organ, or a population of implanted cells that produce the replacement protein). Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Any of the formulations described above can be administered in these methods. The composition may be administered at the rate of about 10 µg to 10 mg per day per kg of body weight; one method of administration may consist of using solutions or suspensions containing approximately from 0.01 mg to 1 mg of active substance per ml. The compounds may be administered at the rate of about 10, 20, 30, 40, 50, 60, 70, 80, 90, or 100 µg to 1, 2, 3, 4, 5, 6, 7, 8, 9, or 10 mg per day per kg of body weight; in one aspect, solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml may be used.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating liver injury following a Kasai procedure in an individual in need thereof, comprising administering a C1-Inhibitor ("C1-INH") to said individual, wherein said C1-INH is selected from recombinant C1-INH, plasma-derived C1-INH, and combinations thereof.

2. The method of claim 1, wherein said administration promotes a regenerative response in a liver cell in said individual.

3. The method of claim 1, wherein said administration preserves, restores, or improves liver function in said individual.

4. The method of claim 1, wherein said administration reduces the need for a liver transplant in said individual.

5. The method of claim 1, wherein said C1-INH is administered at a dose of from about 1 mg/kg to about 10 mg/kg.

6. The method of claim 1, wherein said C1-INH is administered in an amount sufficient to reduce serum biomarkers of liver injury selected from ALT, AST and/or Bilirubin.

7. The method of claim 1, wherein said C1-INH is administered until improvement in a phenotypic outcome occurs.

8. The method of claim 1, wherein said C1-INH is administered via a route selected from one or both of intravenously and subcutaneously.

* * * * *